United States Patent
Moehring et al.

(10) Patent No.: US 10,568,515 B2
(45) Date of Patent: Feb. 25, 2020

(54) OPTICAL COHERENCE TOMOGRAPHY DEVICE FOR OTITIS MEDIA

(71) Applicant: OtoNexus Medical Technologies, Inc., Seattle, WA (US)

(72) Inventors: Mark A. Moehring, Seattle, WA (US); Jay A. Chesavage, Palo Alto, CA (US)

(73) Assignee: OtoNexus Medical Technologies, Inc., Seattle, WA (US)

( * ) Notice: Subject to any disclaimer, the term of this patent is extended or adjusted under 35 U.S.C. 154(b) by 387 days.

(21) Appl. No.: 15/188,750

(22) Filed: Jun. 21, 2016

(65) Prior Publication Data

US 2017/0360302 A1    Dec. 21, 2017

(51) Int. Cl.
*A61B 5/12*    (2006.01)
*A61B 5/00*    (2006.01)

(52) U.S. Cl.
CPC .............. *A61B 5/0066* (2013.01); *A61B 5/12* (2013.01); *A61B 5/412* (2013.01); *A61B 5/6817* (2013.01); *A61B 5/7278* (2013.01)

(58) Field of Classification Search
CPC ................ A61B 5/0066; A61B 5/6817; A61B 5/12–126
See application file for complete search history.

(56) References Cited

U.S. PATENT DOCUMENTS

| | | | |
|---|---|---|---|
| 5,115,133 A | 5/1992 | Knudson et al. | |
| 5,321,501 A | 6/1994 | Swanson et al. | |
| 5,383,467 A | 1/1995 | Auer et al. | |
| 6,950,692 B2 | 9/2005 | Gelikonov et al. | |
| 7,632,232 B2 | 12/2009 | Lewandowski et al. | |
| 7,751,057 B2 | 7/2010 | Oldenburg et al. | |
| 8,115,934 B2 | 2/2012 | Boppart et al. | |
| 8,594,757 B2 | 11/2013 | Boppart et al. | |
| 9,014,792 B2 | 4/2015 | Goldfain et al. | |
| 9,364,148 B2 | 6/2016 | Roberts | |
| 9,788,712 B2 | 10/2017 | Seth et al. | |
| 9,867,528 B1 | 1/2018 | Boppart et al. | |
| 9,918,622 B2 | 3/2018 | Seth et al. | |

(Continued)

FOREIGN PATENT DOCUMENTS

| WO | WO-2017222947 A1 | 12/2017 |
|---|---|---|
| WO | WO-2018222782 A1 | 12/2018 |

OTHER PUBLICATIONS

Co-pending U.S. Appl. No. 16/043,584, filed Jul. 24, 2018.

(Continued)

*Primary Examiner* — George R Evanisko
(74) *Attorney, Agent, or Firm* — Wilson Sonsini Goodrich & Rosati (57) ABSTRACT

An OCT apparatus and method for characterization of a fluid adjacent to a tympanic membrane has a low coherence source which is coupled to a splitter which has a measurement path and a reference path. The reference path is temporally modulated for length, and the combined signals from the reference path and the measurement path are applied to a detector. The detector examines the width of the response and the time variation when an optional excitation source is applied to the tympanic membrane, the width of the response and the time variation forming a metric indicating the viscosity of a fluid adjacent to the tympanic membrane being measured.

12 Claims, 5 Drawing Sheets

(56) References Cited

U.S. PATENT DOCUMENTS

| | | | |
|---|---|---|---|
| 1,035,716 | A1 | 7/2019 | Jay et al. |
| 2003/0171655 | A1 | 9/2003 | Newman et al. |
| 2005/0059868 | A1 | 3/2005 | Schurman |
| 2006/0282009 | A1 | 12/2006 | Oberg et al. |
| 2007/0112273 | A1 | 5/2007 | Rogers et al. |
| 2009/0037922 | A1 | 2/2009 | Herington |
| 2009/0185191 | A1* | 7/2009 | Boppart ............... A61B 5/0066 356/479 |
| 2011/0286505 | A1 | 11/2011 | Hedley |
| 2013/0165763 | A1 | 6/2013 | Huang et al. |
| 2013/0342826 | A1 | 12/2013 | Goldfain et al. |
| 2014/0249426 | A1 | 9/2014 | Huh et al. |
| 2014/0316278 | A1 | 10/2014 | Addison et al. |
| 2015/0169435 | A1 | 6/2015 | Wu |
| 2016/0007840 | A1 | 1/2016 | Boppart et al. |
| 2017/0014053 | A1 | 1/2017 | Moehring et al. |

OTHER PUBLICATIONS

"PCT/US17/38052 International Search Report dated Oct. 24, 2017."
Office Action dated Jul. 6, 2018 for U.S. Appl. No. 15/609,015.
Sorrell et al., Bacteria Identification of Otitis Media with Fluorescence Spectroscopy, Lasers in Surgery and Medicine, 14:155-163 (1994).
Spector et al., Noninvasive Fluorescent Identification of Bacteria Causing Acute Otitis Media in a Chinchilla Model, The Laryngoscope, 110:1119-1123 (2000).

* cited by examiner

*Figure 1*

Optical Coherence Tomography Tympanic Membrane Characterization

*Figure 2A*
Mech Drvr

*Figure 2B*
Mech Drvr

*Figure 3*
Optical Coherence Tomography Tympanic Membrane Characterization

*Figure 4*
Multi-wavelength Detector

Figure 6
Optical Waveguide system for OCT measurement of TM

Figure 7

Optical Waveguide system for OCT measurement of TM

OPTICAL COHERENCE TOMOGRAPHY DEVICE FOR OTITIS MEDIA

FIELD OF THE INVENTION

The present invention relates optical coherence tomography (OCT). In particular, the device relates to OCT for use in the diagnosis of otitis media (OM).

BACKGROUND OF THE INVENTION

Otitis Media is a common disease of the inner ear, involving tissue inflammation and fluidic pressure which impinges on the tympanic membrane. Otitis Media may be caused by a viral infection, which generally resolves without treatment, or a bacterial infection, which may progress and cause hearing loss or other deleterious and irreversible effects. Unfortunately, it is difficult to distinguish between viral or bacterial infection using currently available diagnostic devices, and the treatment methods for the two underlying infections are quite different. For bacterial infections, antibiotics are the treatment of choice, whereas for viral infections, the infection tends to self-resolve, and antibiotics are not only ineffective, but may result in an antibiotic resistance which would make them less effective in treating a subsequent bacterial infection.

The definitive diagnostic tool for inner ear infections is myringotomy, an invasive procedure which involves incisions into the tympanic membrane, withdrawal of fluid, and examining the effusion fluid under a microscope to identify the infectious agent in the effusion. Because of complications from this procedure, it is only used in severe cases. This presents a dilemma for medical practitioners, as the prescription of antibiotics for a viral infection is believed to be responsible for the evolution of antibiotic resistance in bacteria, which may result in more serious consequences later in life, and with no efficacious result, as treatment of viral infectious agents with antibiotics is ineffective. An improved diagnostic tool for the diagnosis of otitis media is desired.

OBJECTS OF THE INVENTION

A first object of the invention is a non-invasive medical device for the identification of fluid type adjacent to a tympanic membrane.

A second object of the invention is a method for identification of a fluid adjacent to a tympanic membrane.

A third object of the invention is a method for performing optical coherence tomography for identification of a film characteristic adjacent to a tympanic membrane.

A fourth object of the invention is an apparatus for performing optical coherence tomography for identification of a fluid characteristic adjacent to a tympanic membrane.

A fifth object of the invention is an apparatus and method for characterization of a tympanic membrane and adjacent materials by coupling a pressure excitation source to a tympanic membrane, where the tympanic membrane is illuminated through a measurement path by an optical source having low coherence, the low coherent optical source also coupled to a reference path and to a mirror, where reflections from the mirror and reflections from the tympanic membrane are summed and presented to a detector, the reference path length modulated over a range which includes the tympanic membrane, the detector thereby receiving reflected optical energy from the tympanic membrane through the measurement path and also from the mirror through the reference path, such that modulation of the reference path length at a sufficiently high rate allows for estimation of the tympanic membrane position in response to the pressure excitation, thereby providing characterization of the tympanic membrane and adjacent fluid.

A sixth object of the invention is an optical coherence tomography system having a measurement path and a reference path, the reference path modulated in length, the measurement path and reference path coupled through an optical splitter to an optical source having low coherence, where reflected optical energy from the reference optical path and reflected optical energy from the measurement optical path are summed and provided to a wavelength splitter and thereafter to a plurality of detectors, one detector for each sub-range of wavelengths within the wavelength spectrum of the low coherence optical source, the plurality of detectors coupled to a controller discriminating by wavelength characteristics the detector response for at least two different reflective materials.

SUMMARY OF THE INVENTION

An optical coherence tomography (OCT) device has a low coherence optical source generating optical energy coupled through a first splitter, thereafter to a second splitter, the second splitter having a measurement optical path to a tympanic membrane and also a reference optical path to a reflector which returns the optical energy to the first splitter, where the reflected optical energy is added to the optical energy reflected from the measurement optical path. The combined reflected optical energy is then provided to the first splitter, which directs the optical energy to a detector. The reflector is spatially modulated in displacement along the axis of the reference optical path such that the detector is presented with an optical intensity and optionally a continuum of optical spectral density from a particular measurement path depth, when the measurement optical path and reference optical path are equal in path length. When the device is positioned with the measurement path directed into an ear canal and directing optical energy to a tympanic membrane, by varying the reference optical path length through translation of the location of the reflector along the axis of the reference optical path, a measurement of optical and spectral characteristics of the tympanic membrane may be performed. Additionally, an external pressure excitation may be applied to provide an impulsive or steady state periodic excitation of the tympanic membrane during the OCT measurement, and a peak response and associated time of the peak response identified. The temporal characteristics and positional displacement of the tympanic membrane can be thereafter examined to determine the tympanic membrane response to the external pressure excitation. The evaluation of the tympanic membrane response from the OCT detector data may subsequently be correlated to a particular viscosity or biofilm characteristic. By examination of the temporal characteristic, an estimate of the viscosity of a fluid adjacent to a tympanic membrane may be determined, and the viscosity subsequently correlated to the likelihood of a treatable bacterial infection.

DETAILED DESCRIPTION OF THE INVENTION

Figure 1:
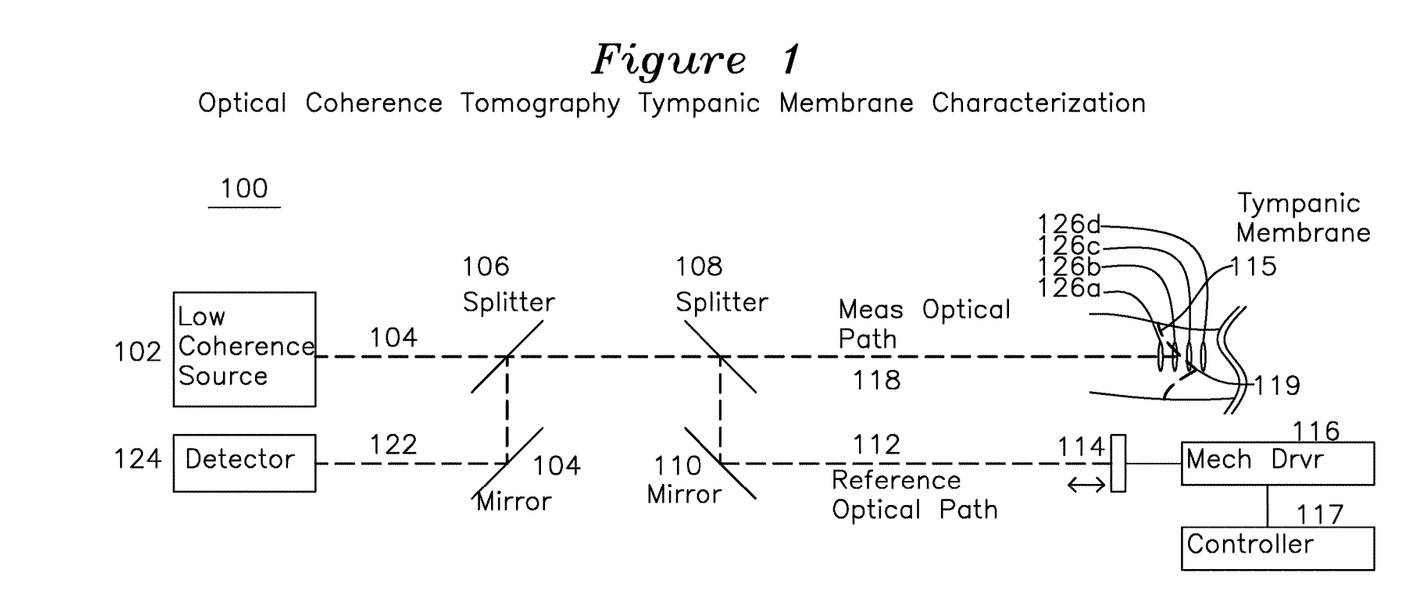
FIG. 1 shows a block diagram of an optical coherence tomography characterization system.

FIG. 1 shows a block diagram for an optical coherence tomography (OCT) device according to one example of the invention. Each reference number which appears in one drawing figure is understood to have the same function when presented in a different drawing figure. A low coherence source 102 such as a broadband light emitting diode (LED) with a collimated output generates optical energy along path 104 to first optical splitter 106, and optical energy continues to second optical splitter 108, where the optical energy divides into a measurement optical path 118 and a reference optical path 112, which include the segment from second splitter 108 to mirror 110 to path length modulator 114. The optical energy in the measurement optical path 118 interacts with the tympanic membrane 120, and reflected optical energy counter-propagates to the detector via path 118, where it is joined by optical energy from reference optical path 112 reflected from mirror 110 and splitter 108, and the combined reflected optical energy propagates to first splitter 106, thereafter to mirror 105, and to detector 124 via path 122. Detector 124 generates an electrical signal corresponding to the intensity of detected optical energy on path 122, which is a steady state maximum when the path length for reflected optical energy from the tympanic membrane is exactly the same length as the reference optical path, and a temporal maximum if the reference optical path length is swept over a range, such as by actuating path length modulator 114 over time. Each type of reflective membrane will produce a characteristic detector signal. For example, as the reference path length traverses through a thin membrane boundary such as a healthy tympanic membrane, a single peak will result corresponding to the single reflective region of the tympanic membrane. If the reference path length is through a fluidic ear such as one containing low-viscosity infectious effusion, an initial peak of the tympanic membrane reflection will subsequently generate a region of extended reflection with an amplitude that drops from optical attenuation of the reflected signal. If the reference path length traverses through the tympanic membrane with a bacterial infection, a bacterial film may be present on the opposite surface of the tympanic membrane, which may produce a greater axial extent of reflection, followed by a pedestal indicating a high scattering coefficient and corresponding increased attenuation. Additionally, the three types of fluid viscosities behind the tympanic membrane (air vs thin fluid vs thick fluid) will respond differently to pressure excitations generated on the tympanic membrane. Accordingly, is possible to modulate the reference optical path length and optionally the pressure adjacent to the tympanic membrane, and examine the nature of the detector output signal and response to excitation pressure to determine the presence or absence of fluid adjacent to the tympanic membrane, the presence or absence of a biofilm such as bacteria adjacent to the tympanic membrane, and the viscosity of fluid adjacent to the tympanic membrane, all from movement of the tympanic membrane on the measurement optical path as presented at the detector output.

In one example of the present invention, the path length modulator 114 varies the reference path length by a distance corresponding to the measurement path length from 126a to 126d of FIG. 1, corresponding to a region of movement of a tympanic membrane 115 to be characterized. As modulator 114 increases the reference path length, the signal delivered to the detector is closer to region 126d and when modulator 114 decreases the distance of the reference path length, the region signal delivered to the detector is in region 126a.

Figure 2A:
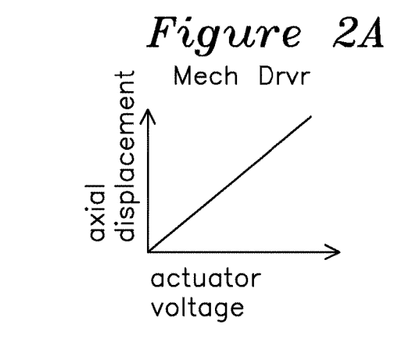
FIG. 2A shows a plot of mechanical actuator displacement vs actuator voltage.

FIG. 2A shows an example relationship between actuator voltage or current and axial displacement of path length modulator 114, which is driven by a mechanical driver circuit 116, which may be a voice coil driver for a voice coil actuator coupled to mirror 114, modulating the mirror about the optical axis of 112. The type of driver and path length modulator 114 is dependent on the highest frequency of displacement modulation, since the energy to displace path length modulator 114 is related to the mass of the path length modulator 114, such as the case of a moving mirror. The mirror and actuator may be micro electrical machined system (MEMS) for lower reflector mass and correspondingly faster mirror response. It may be possible to utilize a variety of other path length modulators without limitation to the use of mirrors.

Figure 2B:
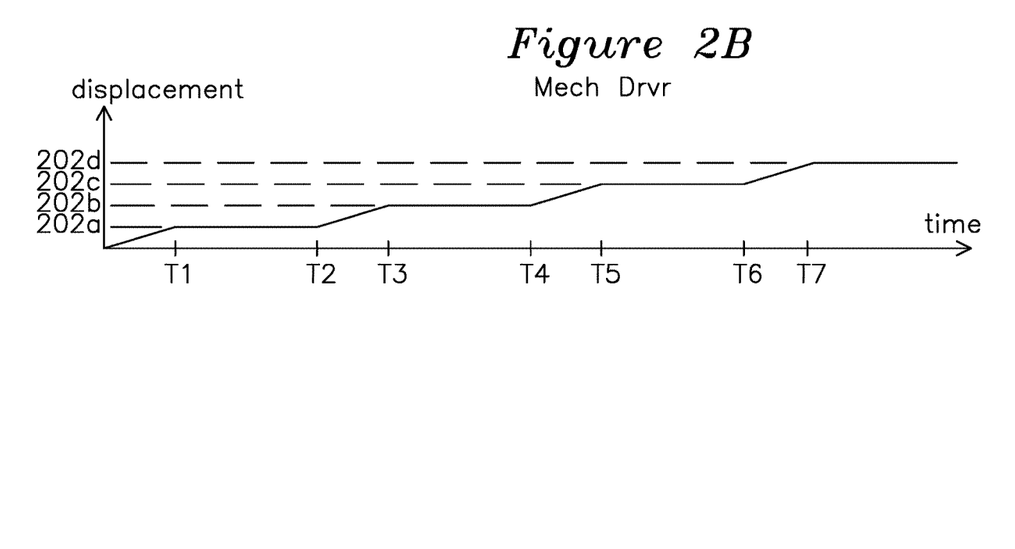
FIG. 2B shows a plot of reference path length over time, as controlled by actuator voltage or current.

FIG. 2B shows the controller 117 generating an actuator voltage in a step-wise manner, with the actuator stopping momentarily at each depth. For example, if increased actuator drive results in a longer reference path length, then from T1 to T2, the actuator voltage may be 202a, corresponding to the displacement position 126a of FIG. 1, and the other voltages 202b, 202c, and 202d may correspond to positions adjacent to the tympanic membrane of 126b, 126c, and 126d, respectively.

Figure 3:
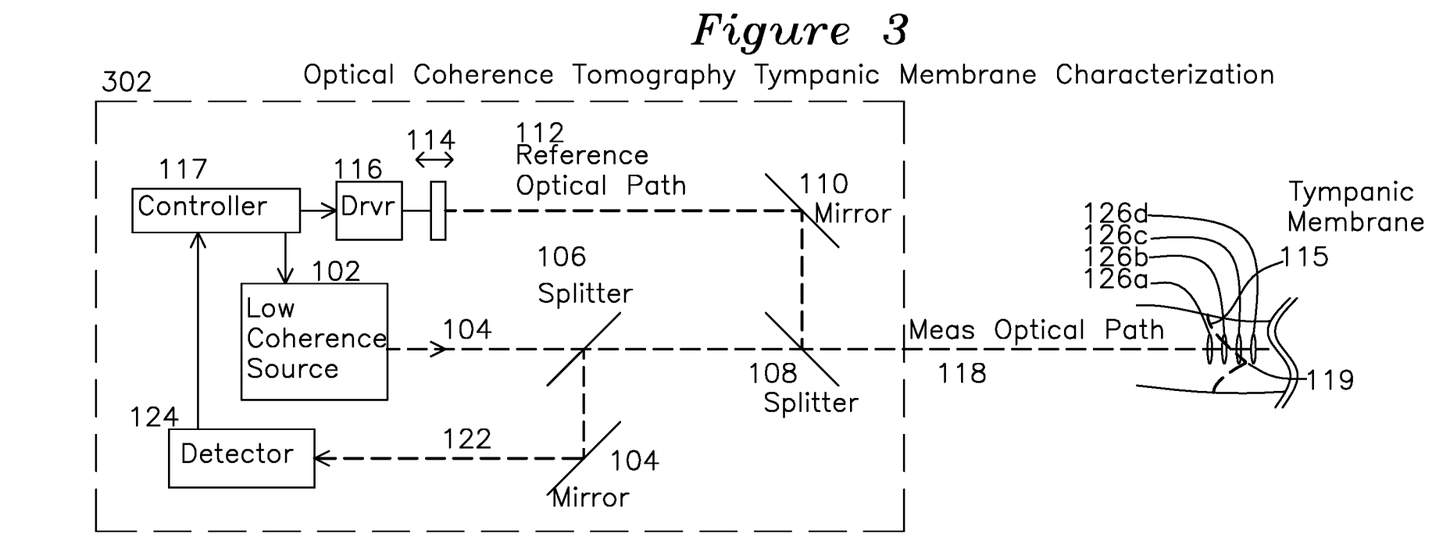
FIG. 3 shows a block diagram for an optical coherence tomography characterization system for use examining a tympanic membrane.

FIG. 3 shows an example OCT tympanic membrane characterization system 302 with the elements arranged to provide a single measurement output. For the case of free-space optics (optical energy which is not confined within a waveguide such as an optical fiber), the system splitters and combiners of FIGS. 1 and 3 are partially reflective mirrors. The principal elements show in FIG. 3 correspond to the same functional elements of FIG. 1. By rearrangement of the reference optical path, the elements of the system may be enclosed, as shown.

Figure 4:
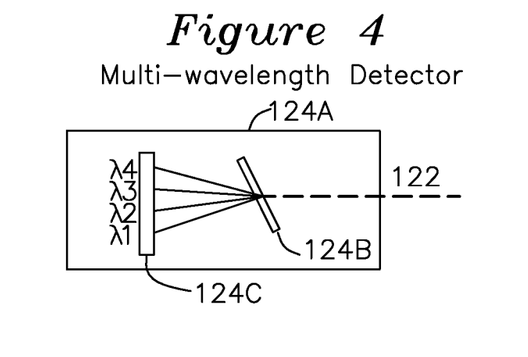
FIG. 4 shows a polychromatic detector.

In one example of the invention, detector 124 may be a single omni-wavelength optical detector responsive to the total applied optical intensity, and having a characteristic response. In another example of the invention detector 124 may include a single wavelength filter, or a chromatic splitter and a plurality of detector elements, such that each reflected optical wavelength may be separately detected. FIG. 4 shows collimated optical energy 122 entering chromatic detector 124A, where it is split into different wavelengths by refractive prism 124B, which separates the wavelengths λ1, λ2, λ3, λ4 onto a linear or 2D detector 124C, which is then able to provide an intensity map for the reflected optical energy by wavelength. Individual detection of wavelengths may be useful where the signature of wavelength absorption is specific to a particular type of bacteria or tympanic membrane pathology. The spectrum of detector response is typically tailored to the reflected optical energy response, which may be in the IR range for an OCT system with more than a few mm of depth measurement capability. In one example of the invention, the detector spectral response for various biological materials is maintained in a memory and compared to the superposition of responses from the plurality of optical detectors. For example, the optical reflective characteristics of cerumen (earwax), a healthy tympanic membrane, an inflamed tympanic membrane (a tympanic membrane which is infused with blood), a bacterial fluid, an effusion fluid, and an adhesive fluid may be maintained in a template memory and compared to the spectral distribution of a measured tympanic membrane response over the axial depth of data acquisition. The detector response at each axial depth over the range of reference optical path length can then be compared to the spectral characteristics of each of the template memory spectral patterns by a controller, with the controller examining the detector responses for each wavelength and the contents of the template memory and estimating the type of material providing the measurement path reflection based on this determination. The detection of a spectral pattern for cerumen may result in the subtraction of a cerumen spectral response from the detector response, and/or it may result in an indication to the user that earwax has been detected in the response, which the user may eliminate by pointing the measurement optical path in a different region of the tympanic membrane.

Because the axial resolution of the optical coherence tomography is fractions of an optical wavelength, it is possible to characterize each of the structures separately on the basis of optical spectrum, even though each of the structures being imaged is only on the order of a hundred microns in axial thickness. The axial resolution of the system may be improved by providing a very narrow optical beam with high spatial energy along the measurement axis and over the axial extent of the tympanic membrane.

Figure 5A:
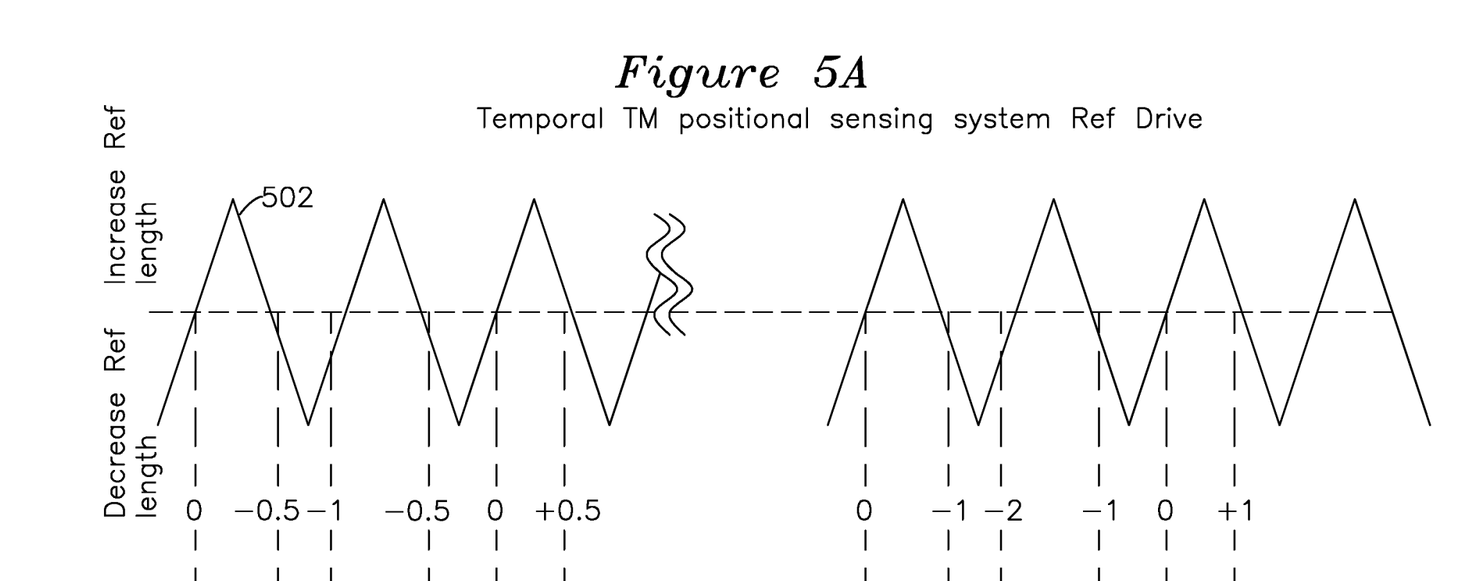
FIG. 5A shows a plot of an example excitation waveform for modulation of a reference length
Figure 5B:
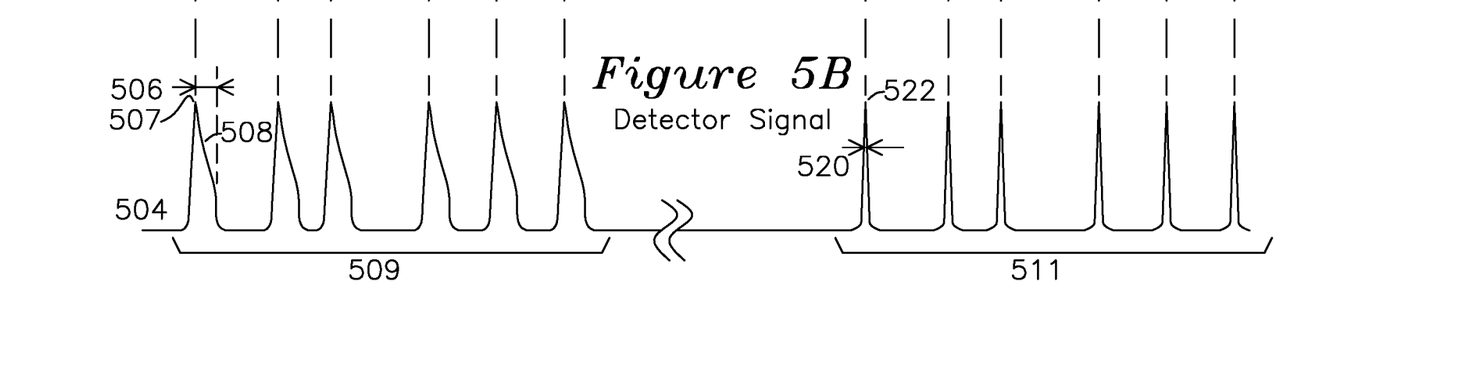
FIG. 5B shows a detector signal for a tympanic membrane adjacent to fluid such as from OME and a detector signal for a normal tympanic membrane.

FIGS. 5A and 5B show an example of the invention for use in detecting position of a tympanic membrane over time. The controller 117 generates a triangle waveform 502 for use by the path length modulator, which directs the optical energy to the tympanic membrane, which may have fluid adjacent to it, and the fluid may have a particular viscosity, which may be known to increase during the progression of a bacterial infection. Bacterial infections are known to provide a biological film on the surface of a membrane, such as the tympanic membrane, with specific optical reflection characteristics. The optical signal is directed through the outer ear canal towards the tympanic membrane to be characterized, and the detector responses of FIG. 5B are examined by controller 117 of FIG. 3. A first set of waveforms 509 shows a time domain response which includes an initial peak 507 associated with the strong reflection of the sharp reflective optical interface provided by the tympanic membrane at a first reflective interface, and the fluid behind the tympanic membrane also generates a signal which attenuates with depth, shown as a sloped pedestal 508. The presence of pedestal 508 indicates the presence of fluid behind the tympanic membrane. This may be contrasted with the second set of responses 511 for a normal tympanic membrane, such as the peak of waveform 522, which is comparatively narrow and of shortened duration 520, as reflective fluid is not present behind the tympanic membrane.

In an additional embodiment of the invention, the tympanic membrane itself may be modulated by an external excitation source, such as an air puff, or a source of air pressure which is modulated over time. Where an external pressure excitation source is provided, and the pressure excitation is selected to provide less than 1% displacement of the tympanic membrane, for example, the relative temporal position of the peak optical signal will indicate the position of the tympanic membrane. Because the refresh rate of the system is optical, rather than acoustic of prior art ultrasound devices, the speed of interrogation of the tympanic membrane is only limited by the rate of modulation of the path length modulator 114, which may be several orders of magnitude faster than an ultrasound system. Additionally, the axial resolution of an optical system relying on optical interferometry is much greater than the axial resolution of an ultrasound system which is governed by transducer ringdown. Additionally, because the acoustic impedance boundary between air and the tympanic membrane is extremely large, the ultrasound penetration depth of ultrasound to structures beyond the tympanic membrane is very limited. By contrast, the optical index of refraction ratio from air to tympanic membrane is many orders of magnitude lower than the ultrasound index of refraction ratio across this boundary, so the optical energy loss at the interface is lower. The optical penetration is primarily bounded by the scattering losses associated with the tympanic membrane and structures beyond the tympanic membrane interface, and these losses may be mediated in part by using a very high optical energy which is pulsed with a duty cycle modulation to maintain the average power applied to the tympanic membrane in a reasonable average power range.

Figure 6:
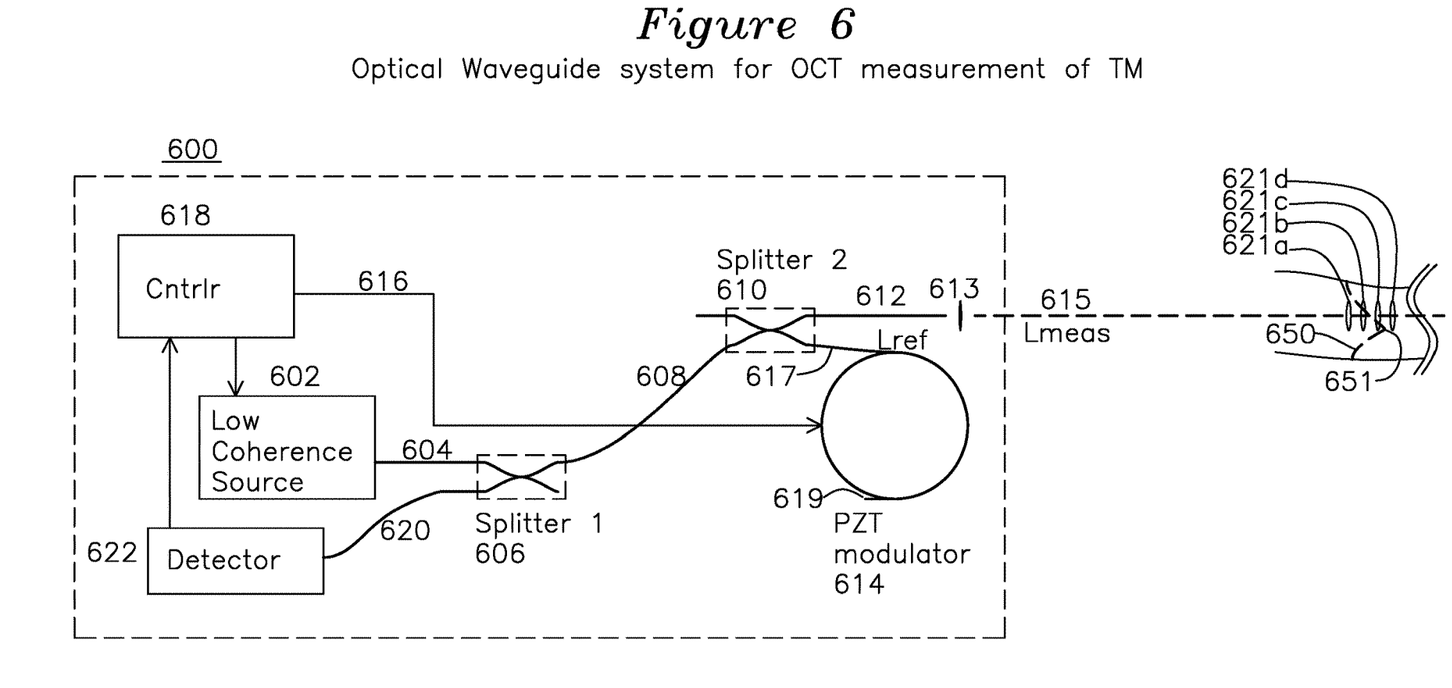
FIG. 6 shows an optical waveguide system for measurement of a tympanic membrane.

FIG. 6 shows a fiber-optic example of an optical coherence tomography system 600. Controller 618 coordinates the various subsystems, including enabling low coherence source 602, which couples optical energy to an optical fiber 604, which delivers this optical energy thereafter to a first splitter 606, thereafter to optical fiber 608 and to second splitter 610. Optical energy from second splitter 610 is directed down two paths, one a measurement path 612 with length Lmeas 615 to a tympanic membrane, and the other to reference optical path 617 with length Lref and terminating into an open reflective fiber end 619, which may alternatively be a mirrored polished end or optical reflective termination, with the optical path 617 including an optical fiber wrapped around a PZT modulator 614, which changes dimensional shape and diameter when an excitation voltage is applied to the PZT. When the PZT modulator 614 is fed with a sine wave or square wave excitation, the PZT modulator 614 increases and decreases in diameter, thereby providing a variable length Lref. The PZT modulator 614 is also capable of high speed fiber length modulation in excess of 100 Khz in frequency. Other fiber length modulators known in the art may be used for rapidly changing the length of optical fiber on the Lref path, with the PZT modulator 614 shown for reference only. The combined optical energy from the Lmeas path and Lref path reach the second splitter 610 and return on fiber 608, comprising the sum of optical energy reflected from PZT modulator 614 and reflected from the tympanic membrane 650. The combined optical energy travels down path 608 to first splitter 606, through fiber 620, and to detector 622, where the coherent optical energy superimposes and subtracts, forming a detector 622 output accordingly, which is fed to the controller 618 for analysis.

The controller 618 also generates the PZT modulator excitation voltage 616, such as the voltage or current waveform 502 of FIG. 5A, and may also generate a signal to enable the low coherence source 602, and perform analysis of the detector 622 response, which may be a single intensity value over the wavelength response of the detector 622, or the individual wavelength output provided by the sensor of FIG. 4. The controller acts on the detector responses in combination with the Lref modulation function to determine an effusion metric which may be correlated to the likelihood of fluid being present adjacent to a tympanic membrane, and also provide an indication of the viscosity of the fluid adjacent to the tympanic membrane.

Figure 7:
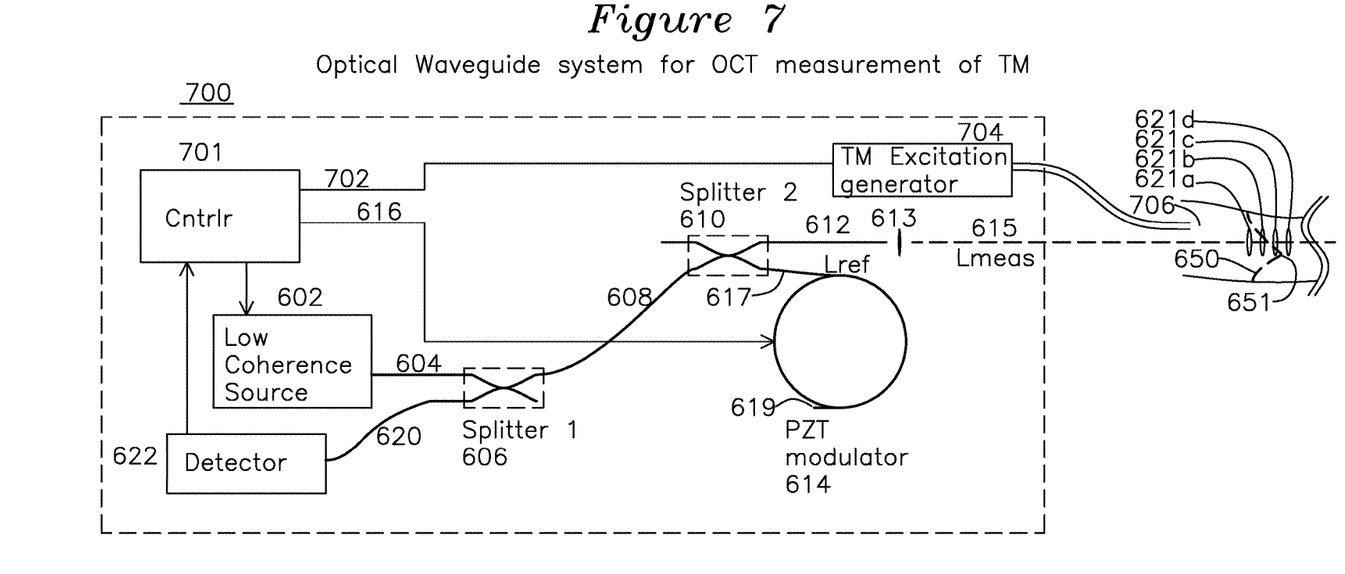
FIG. 7 shows an optical waveguide system for measurement of a tympanic membrane with an excitation source.

FIG. 7 shows an extension of FIG. 6 with an external tympanic membrane excitation generator 704 which delivers miniscule pressure changes such is actuated by a voice coil actuator or other pressure source, preferably with peak pressures below 50 deka-pascals (daPa) for application to a tympanic membrane. The modulation of the reference path length by the PZT modulator 614 is at a rate which exceeds the highest frequency content of the excitation generator 704 by at least a factor of 2 to satisfy the Nyquist sampling requirement.

In one example of the invention, the reference path length is modulated by a first modulator and second modulator operative sequentially, where the first modulator provides a large but comparatively slow reference path length change, and the second modulator provides a small but comparatively fast reference path length change. In this manner, the first modulator is capable of placing the region of OCT examination within a region of interest such as centered about a tympanic membrane, and the second modulator is capable of quickly varying the path length to provide a high rate of change of path length (and accordingly, a high sampling rate) for estimation of tympanic membrane movement in response to the pressure excitation.

It can be seen in the tympanic membrane shown as 115 in FIGS. 1 and 3, and 650 in FIGS. 6 and 7, that the tympanic membrane has a conical shape with a distant vertex (119 of FIGS. 1 and 3, 651 of FIGS. 6 and 7), which is known in otolaryngology as the "cone of light", as it is the only region of the tympanic membrane during a clinical examination which provides a normal surface to the incident optical energy. Similarly, when using an ultrasonic source of prior art systems, the cone of light region is the only part of the tympanic membrane which provides significant reflected signal energy. The optical system of the present invention is operative on the reflected optical energy from the surface, which need not be normal to the incident beam for scattered optical energy, thereby providing another advantage over an ultrasound system.

Figure 8A:
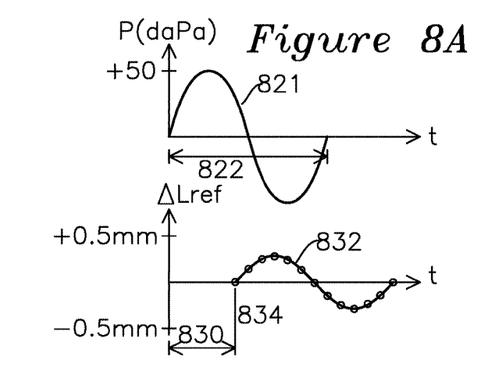
FIG. 8A shows a plot for a sinusoidal excitation applied to deformable surface or membrane with a reflected response signal.

FIG. 8A shows an example sinusoidal pressure excitation from excitation generator 704 applied to a tympanic membrane, such as a sinusoidal waveform 821 applied using a voice coil diaphragm actuator displacing a volume sufficient to modulate a localized region of the tympanic membrane or surface pressure by 100 daPa (dekapascals) p-p. Sub-sonic (below 20 Hz) frequencies may require sealing the localized region around the excitation surface, whereas audio frequencies (in the range 20 Hz to 20 kHz) and super-audio frequencies (above 20 kHz) may be sufficiently propagated as audio waves from generator 704 without sealing the ear canal leading to the tympanic membrane to be characterized. The sinusoidal pressure excitation 821 results in a modulation of the surface, which is shown as plot 832, as the modulation in surface position corresponds to a change in the associated Lref path length by the same amount. Each discrete circle of waveform 832 represents a sample point from the OCT measurement system 700, corresponding to the Lref path length and change in tympanic membrane position, with each point 332 representing one such sample. In one example embodiment of the invention, a series of sinusoidal modulation excitation 821 frequencies are applied, each with a different period 822, and the delay in response 830 and peak change in Lref are used in combination to estimate the ductility or elasticity of the tympanic membrane, fluid viscosity, or other tympanic membrane or fluid property. In the present examples, there is a 1:1 relationship between the displacement of the tympanic membrane and associated change in path length of the reference path which results in the peak response. For example, if the scale of FIG. 5B is a sequence of 0, −0.5 mm, −1 mm, −0.5 mm, 0 mm, 0.5 mm, etc, then this represents a corresponding displacement in the tympanic membrane by these same distances. By applying a series of audio and sub-audio tones with various cycle times 822 and measuring the change in Lref as shown in plot 832, it is possible to estimate the displacement of the tympanic membrane and extract frequency dependent characteristics such as viscosity or elasticity of the fluid behind the tympanic membrane. For example, an exemplar elasticity metric measurement associated with the changed density or viscosity of the fluid could be an associated change in surface or membrane response time 874 for a step change, or phase delay 830 for a sinusoidal frequency. In this manner, a frequency domain response of the surface may be made using a series of excitations 821 and measuring a series of surface responses 832. The reference path modulator 614 of FIGS. 6 and 7, or mirror 114 of FIG. 3, may include a first path length modulator which centers the reference path length to include the tympanic membrane, and a second path length modulator which rapidly varies the reference path length to provide adequate sampling of the axial movement of the tympanic membrane.

Figure 8B:
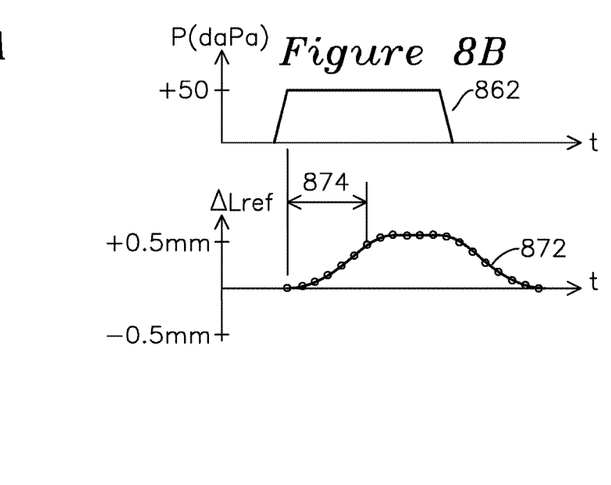
FIG. 8B shows a plot for a step excitation applied to a deformable surface or membrane, and a response to the step excitation.

Whereas FIG. 8A shows a sinusoidal excitation which may be provided in a series of such excitations to generate a phase vs. frequency response plot of the surface displacement from the series of measurements, FIG. 8B shows a time domain step response equivalent of FIG. 8A, where a surface step pressure excitation 862 of 50 daPa peak is applied to the tympanic membrane, which generates the measured tympanic membrane displacement sequence 872. It is similarly possible to characterize the surface response based on a time delay 874 and amplitude response (shown as 0.5 mm) for displacement response plot 872.

In one example of the invention, a separate low-coherence optical source 102 or 602 such as an infrared range source is used for increased penetration depth, and a separate visible source (not shown) is used co-axially to indicate the region of the tympanic membrane being characterized while pointing the measurement optical path onto the tympanic membrane. The optical source 102 or 602 may be an infrared sources to reduce scattering, thereby providing additional depth of penetration. In another example of the invention, the low-coherence optical source 102 or 602 is a visible optical source, thereby providing both illumination of the tympanic membrane region of interest, and also measurement of displacement of the tympanic membrane, as previously described.

The present examples are provided for understanding the invention, it is understood that the invention may be practiced in a variety of different ways and using different types of waveguides for propagating optical energy, as well as different optical sources, optical detectors, and methods of modulating the reference path length Lref. The scope of the invention is described by the claims which follow.

We claim:

1. A method for characterization of a fluid adjacent to a tympanic membrane, the method comprising:

providing a pressure wave modulation using a pressure excitation source, wherein the pressure wave modulation is configured to induce a displacement of the tympanic membrane;

providing optical energy from a low coherence optical source to a first splitter, wherein a first part of the optical energy is directed to a measurement path and a second part of the optical energy is directed to a reference path, wherein the measurement path includes a tympanic membrane to be characterized, wherein a length of the reference path is substantially equal to a length of the measurement path, and wherein the reference path has a reflector for reflecting optical energy;

changing a length of the reference path over periodic intervals, thereby temporally modulating the length of the reference path;

summing reflected optical energy from the measurement path and reflected optical energy from the reference path;

applying the summed optical energy to a detector, wherein the detector provides to a controller a detector peak response as a function of (i) the length of the reference path and (ii) the displacement of the tympanic membrane over time;

examining at the controller a pedestal width of the detector peak response and an arrival time of the detector peak response;

comparing the detector peak response to a reference detector peak response; and forming a tympanic membrane metric from the comparison of the detector peak response and the reference detector peak response, and from the pedestal width and the arrival time of the detector peak response.

2. The method of claim 1, wherein the reference path and the measurement path are free space optic paths formed by fully reflective and partially reflective mirrors.

3. The method of claim 1, wherein the reference path and the measurement path are each formed by a waveguide.

4. The method of claim 1, wherein the reference path and the measurement path are each formed by an optical fiber.

5. The method of claim 1, wherein the low coherence optical source is a light emitting diode.

6. The method of claim 1, wherein the detector is an optical to electrical converter.

7. The method of claim 1, wherein the detector has a plurality of wavelength-specific outputs.

8. The method of claim 7, wherein the method further comprises comparing the plurality of wavelength-specific outputs to wavelength responses of various material types, wherein the wavelength responses are saved in a template memory.

9. The method of claim 8, wherein the wavelength responses saved in the template memory comprise a wavelength response of one of cerumen, a healthy tympanic membrane, an inflamed tympanic membrane, a bacterial fluid, an effusive fluid, or an adhesive fluid.

10. The method of claim 9, wherein the method further comprises providing to a user an indication of a detection of a presence of one of the cerumen, the healthy tympanic membrane, the inflamed tympanic membrane, the bacterial fluid, the effusive fluid, or the adhesive fluid.

11. The method of claim 1, wherein the length of the reference path is modulated by a voice coil actuator coupled to a mirror.

12. The method of claim 1, wherein the length of the reference path is modulated by a PZT activated modulator.

* * * * *